United States Patent [19]

Welker

[11] Patent Number: 5,406,855
[45] Date of Patent: Apr. 18, 1995

[54] SOLENOID ACTUATED SAMPLER

[75] Inventor: Brian H. Welker, Sugar Land, Tex.

[73] Assignee: Welker Engineering Company, Sugar Land, Tex.

[21] Appl. No.: 248,703

[22] Filed: May 25, 1994

[51] Int. Cl.$^6$ ............................................. G01N 1/14
[52] U.S. Cl. ................................................ 73/863.83
[58] Field of Search ............ 73/863.83, 863.84, 864.34, 73/864.35, 864.62, 863.71, 863.72, 863.73, 863.86

[56] References Cited

U.S. PATENT DOCUMENTS

| | | | |
|---|---|---|---|
| 1,837,858 | 12/1931 | Grace | 73/863.84 X |
| 2,370,260 | 2/1945 | Robinson | 73/863.86 X |
| 2,558,387 | 6/1951 | Ray | 73/863.71 X |
| 3,858,449 | 1/1975 | Singer | 73/863.86 X |
| 4,346,611 | 8/1982 | Welker | 73/863.86 |
| 4,562,749 | 1/1986 | Clark | 73/863.84 |
| 4,682,507 | 7/1987 | Terrell | 73/863.83 |
| 4,841,785 | 6/1989 | Welker | 73/863.84 |
| 4,928,536 | 5/1990 | Welker | 73/863.83 |

OTHER PUBLICATIONS

Advertising brochure from Clif Mock Company, Monroe, Texas, Entitled "True-Cut Sampler Systems Model K Series", 20 pages Nov. 1976.
Advertising brochure from Clif Mock Company, Monroe, Texas, Entitled "True-Cut Sampling Systems", 7 pages Oct. 1984.
Informationai Sheet from JisKoot Autocontrol, Ltd., Kent, England entitled "Series 210 Sampler Probe", 2 pages Published by May 1994.
Informational Sheet from JisKoot Autocontrol, Ltd., Kent, England entitled "Internal Sampling Systems-20-0-250-260 Series". 1 page Published by May 1994.
Informational Sheet from JisKoot Autocontrol, Ltd., Kent, England entitled "series 260 Sampler Probe", 2 pages Published by May 1994.
Informational Sheet from Y-Z Industries, Inc., Snyder, Texas entitled "RD-1 Econo-Crude Sampler". 1 page Published by May 1994.

Primary Examiner—Thomas P. Noland
Attorney, Agent, or Firm—Lawrence E. Evans, Jr.; Bruce J. Bowman

[57] ABSTRACT

A fluid pipeline sampler adapted for in-line or by-pass type sampling includes a body having a passage therethrough and a fluid outlet. The sampler is actuated by a pulling-type solenoid in response to an actuating signal. The solenoid shaft is coupled to a yoke that includes a piston mounted on the end opposite the solenoid shaft. The yoke surrounds a valved body extension, and along with the piston and body extension define a sample cylinder. The body extension has a bore that is in fluid communication with the fluid outlet of the main body and the sample cylinder. Initial displacement of the yoke positively causes the piston to trap a sample of known volume within the cylinder. Further displacement injects the trapped sample into the body extension bore that then travels into a sample collector.

8 Claims, 5 Drawing Sheets

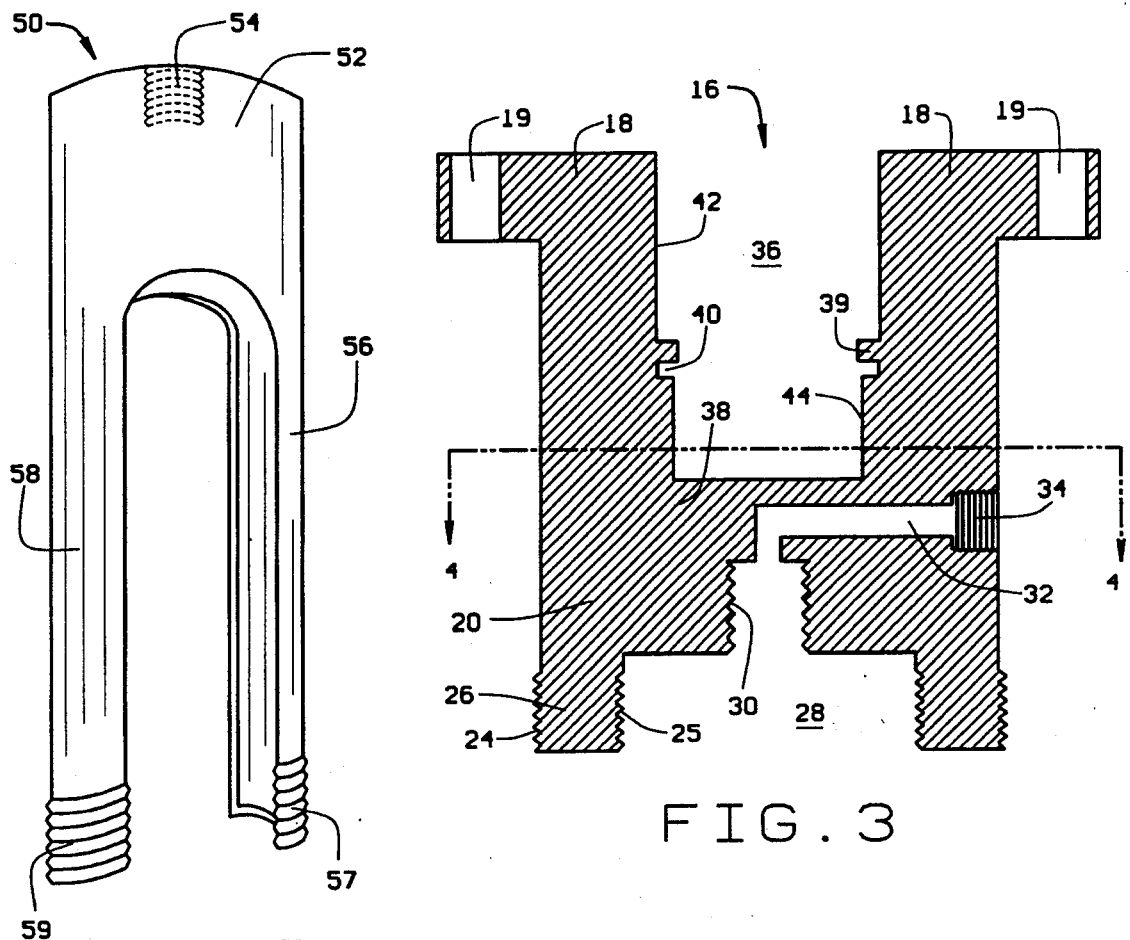
FIG. 5
FIG. 3
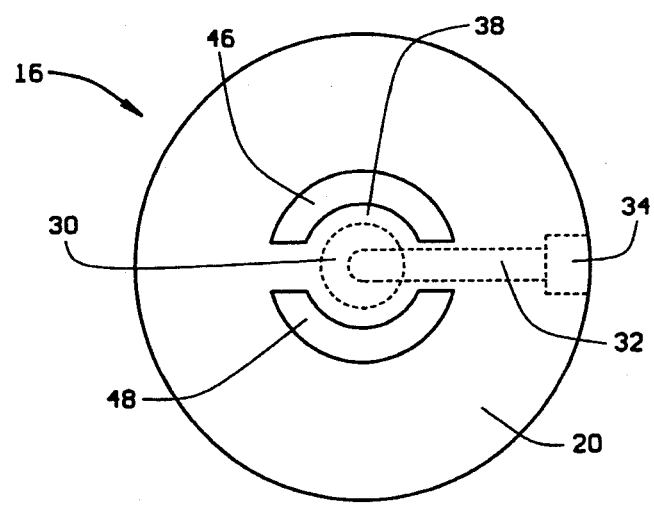
FIG. 4

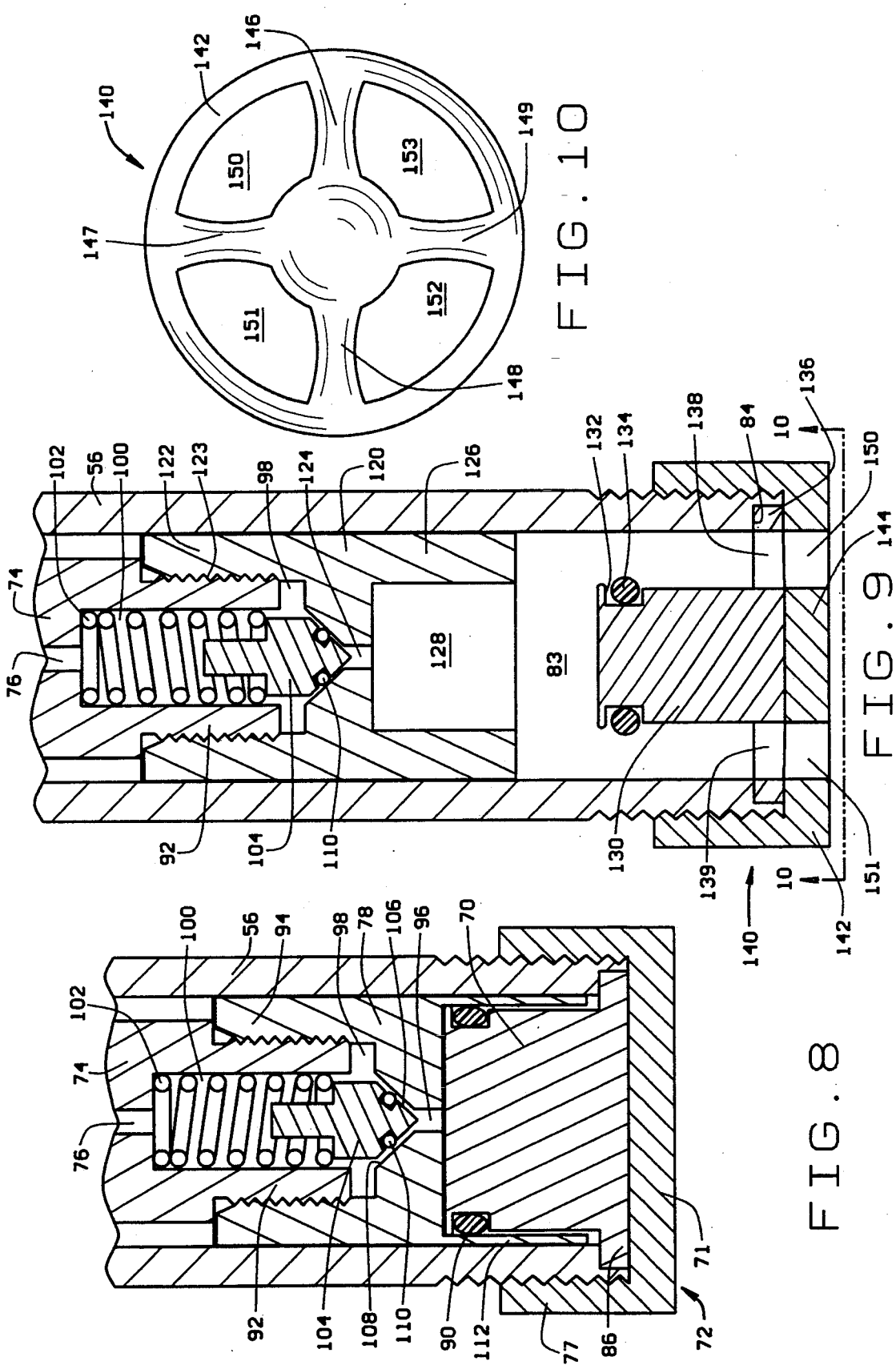

SOLENOID ACTUATED SAMPLER

FIELD OF THE INVENTION

The present invention relates to material samplers and, more particularly to fluid samplers for obtaining a sample of a gas or liquid flowing within a pipe.

It is thus particularly adapted for use with flowing fluids in pipelines of variable pressure, and may be used with a pipeline flow system with high pressures and well as with low pressures. The present sampler is intended for use with gasses and liquids.

BACKGROUND OF THE INVENTION

There is a great need to sample liquids and gasses flowing in pipelines. Substances such as natural gas or oil are priced according to their BTU content, $CO_2$ content, or other variables. A sample must therefor be removed from the pipeline carrying the substance in proportion to the flow in order that an accurate measurement of the variable content per volume unit be obtained. The sample thus obtained is generally caused to be retained in a storage vessel that is coupled to the sampler. The contents of the storage vessel is periodically analyzed by a laboratory. The sample must be collected in proportion to the flow and thus, one part per million or one part per billion may be sampled, stored and assayed to determine price.

The sample storage container may have an internal pressure which is greater or less than the pipeline pressure, and which may vary considerably. Another variable of importance is the portion to be taken to make up the sample.

Also, the reliability of a sampler and the installation point are other important factors regarding samplers. In many situations, the sampler is often installed in remote locations in gas field gathering lines, or perhaps at an intermediate sized pipeline. Such locations are remote and difficult to access. It is also difficult to make complex equipment installation and repair in the field. Therefore, cost, reliability, and complexity are substantially impacted by the present invention.

It is thus desirable to have a simple, easily installed and reliable sampler that can pump a sample into any type of storage container.

SUMMARY OF THE INVENTION

In accordance with the above objects, the present invention provides a simple fluid sampler that is actuated by a pulling shaft type solenoid in response to an actuating signal. The sampler utilizes a reciprocable yoke coupled to the solenoid shaft. The yoke carries the piston that traps a volume of sample within the sample cylinder and injects the sample into a storage vessel as the yoke upwardly travels. Downward travel readies the sampler for another sampling operation.

The sampler may be utilized as an in-line or by-pass type sampler. The provision of less moving parts and a simple design distinguishes the present sampler over the samplers of the prior art.

In one form thereof, the present invention provides an assembly for obtaining a fluid sample from a fluid flowing in a pipeline. The sampler includes a main body defining a first end and a second end with a yoke bore extending from the first end to the second end of the main body, at least a length of the yoke bore defined by oppositely disposed first and second slots. An outlet passage is disposed in the main body, with a yoke reciprocatingly disposed in the yoke bore. The yoke has a first prong and a second prong adapted to be respectively received in the first and second slots, the first and second prongs projecting beyond the second end of the main body. A pulling solenoid is disposed at the first end of the main body, the pulling solenoid having a shaft that is actuatably reciprocable and coupled to the yoke. A body extension is coupled to the second end of the main body radially inwardly of the first and second prongs of the yoke. The body extension has an outlet bore that is in communication with the outlet passage. A cylinder is coupled to an end of the body extension remote from the second end of the main body, the sample cylinder having a restricted opening therein in communication with the outlet. A piston is coupled to an end of the first and second prongs and is adapted to be received in the cylinder when the yoke is upwardly moved by the solenoid shaft. The first and second prongs define a flowthrough passage permitting the fluid flowing in the pipeline to flow therethrough.

The sampler assembly may be further defined by the first and second slots being each arcuate shaped, with the first and second prongs being each arcuate shaped.

BRIEF DESCRIPTION OF THE DRAWINGS

So that the manner in which the above-recited features, advantages, and objects of the present invention are attained and can be understood in detail, a more particular description of the invention, briefly summarized above, may be had by reference to the embodiments thereof which are illustrated in the appended drawings.

It is noted, however, that the appended drawings illustrate only typical embodiments of this invention and is therefore not to be considered limiting of its scope, for the invention may admit to other equally effective embodiments. Reference the appended drawings, wherein:

FIG. 3 is an enlarged sectional side view of the body of the sampler of FIG. 1;

FIG. 4 is a top view of the body taken along line 4—4 of FIG. 3;

FIG. 5 is an enlarged elevational view of the yoke of the present sampler;

FIG. 8 is an enlarged partial sectional front view of the yoke, piston, and cylinder of the present invention depicted in a second stage of sample taking;

FIG. 9 is an enlarged partial sectional front view of a yoke, piston, and cylinder in accordance with another embodiment of the present invention;

FIG. 10 is an enlarged view of the end cap and piston structure taken along line 10—10 of FIG. 9.

DESCRIPTION OF THE PREFERRED EMBODIMENT

Figure 1:
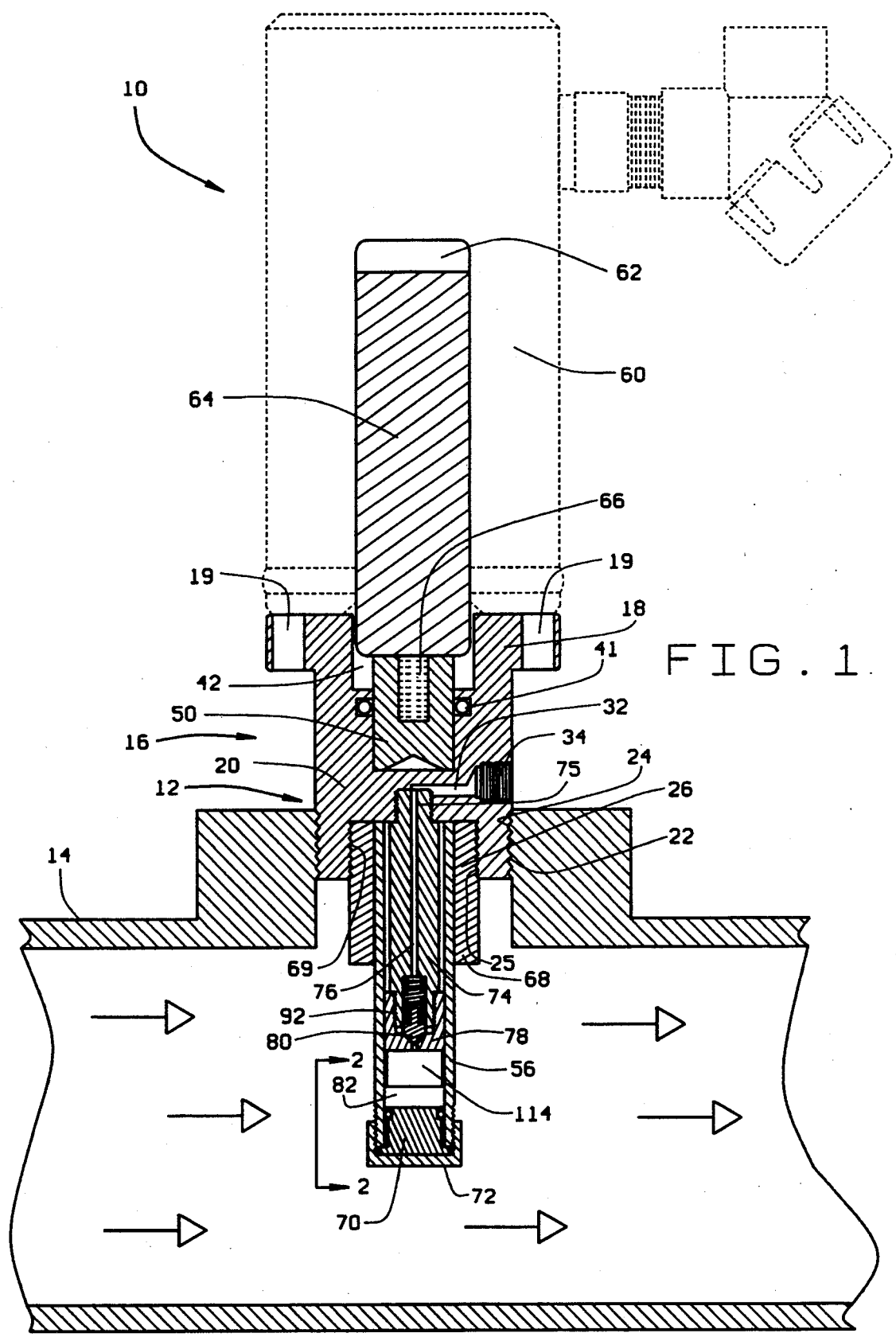
FIG. 1 is a front sectional view of an in-line type sampler in accordance with an embodiment of the present invention disposed in a pipeline carrying a fluid.

Referring now to FIG. 1, there is shown a sampler generally designated 10 extending into an opening 12, such as a weld-o-let, of a pipeline 14 carrying a liquid or gas, the pipeline flow represented by the arrows. The sampler 10 is generally known as an in-line type sampler since at least a portion of the sampler extends into the pipeline fluid flow. With additional reference to FIG. 3, the sampler 10 includes a main body 16, preferably formed from aluminum or other similar material. The main body 16 defines an upper portion 18 and a lower portion 20. The upper portion 18 includes a plurality of mounting bores generally designated 19. The mounting bores 19 are adapted to receive screws, bolts or the like for attaching the body 16 to another structure or component. The lower portion 20 includes an annular leg portion 26 having outer threads 24 and inner threads 25. The outer threads 24 are adapted to threadedly attach to threads 22 of the pipe inlet 12 in order to removably mount the sampler 10 relative the pipe 14.

The annular leg portion 26 defines a first annular cavity 28 that is in fluid communication with a threaded opening 30. The threaded opening 30 is oriented along the longitudinal axis of the main body 16 and is concentric with the annular cavity 28. At the axial end of the main body 16 opposite to the cavity 28 is a second cavity 36. The second cavity 36 is defined by a first diameter annular wall 42 and a second diameter annular wall 44, being of a smaller diameter than the first diameter annular wall 42. Disposed at the transition point between the first and second diameter annular walls 42, 44 is an annular ledge 39 that defines an annular groove or channel 40 that is adapted to receive an O-ring 41 (FIG. 1). The first and second cavities 28 and 36 together define an annular center portion 38 with the threaded bore 30 axially extending therein. A passage 32 is disposed transverse to the longitudinal axis of the main body 16 or radially extending from the center portion 38, and is in fluid communication at one end to the threaded bore 30 and at the other end with a threaded outlet 34.

As best depicted in FIG. 4, the center portion 38 of the main body 16 includes a first arcuate channel 46 and a second arcuate channel 48 disposed opposite to the first arcuate channel 46. The first and second arcuate channels 46, 48 are each in communication with the first annular cavity 28 and the second annular cavity 36. Thus, the first annular cavity 28, the first and second arcuate channels 46, 48, and the second annular cavity 36 defines a passage that extends the axial length of the main body 16. At the center portion 38 that passage is divided into two segments, namely the first and second arcuate channels 46 and 48.

Referring back to FIG. 1, a solenoid 60 is disposed on the axial end of the upper portion 18 of the main body 16. The solenoid 60 includes a centrally disposed shaft bore 62 in which is reciprocatingly disposed a solenoid shaft 64. It should be noted that the solenoid 60 is a pulling type solenoid wherein in a rest position the shaft 64 is in a fully downward position and upon actuation, the shaft 64 is upwardly displaced within the limits of the shaft bore 62. The shaft 64 axially extends at least a portion of the distance into the second annular cavity 36. On the axial end of the shaft 64 that extends into the second annular cavity 36 is a threaded stud 66.

Disposed within the passage defined by the first annular cavity 28, the first and second arcuate channels 46, 48, and the second annular cavity 36 is a yoke generally designated 50. Referring in particular to FIG. 5, the yoke 50 is shown. The yoke 50 is preferably fabricated from aluminum, but like the other components of the present invention, a similar material may be used. The yoke 50 includes a top annular portion 52 that has a centrally disposed threaded bore 54 that is adapted to threadedly receive the threaded stud 66 of the solenoid shaft 64. In this manner, the shaft 64 is coupled to the yoke 50 such that the yoke is longitudinally displaced as the shaft 64 is longitudinally displaced by action of the solenoid 60. Axially downwardly extending from the underside of the top annular portion 52 is a first arcuate-shaped leg 56 having threads 57 on the end opposite the top annular portion 52. Also axially downwardly extending from the underside of the top annular portion 52 radially opposite the first leg 56 is a second arcuate-shaped leg 58 having threads 59 on the end opposite the top annular portion 52. The legs 56 and 58 correspond in shape to the first and second arcuate channels 46 and 48 and are thus adapted to respectively extend therethrough. As can be appreciated from the Figures, when the yoke 50 is disposed within the main body 16, the yoke 50 is limited in its downward displacement by the top annular portion 52 abutting or contacting the center portion 38. This position is a normal or flow-through position described hereinbelow under the heading "Operation." As can be appreciated by reference to FIG. 1, the legs 56, 58 of the yoke 50 axially extend a distance from the first annular cavity 28 of the main body 16 and into the pipeline fluid flow.

With continued reference to FIG. 1, the sampler 10 includes a cylindrical stabilizing sleeve 68 that includes threads 69 on an axial end of the sleeve 68. The threads 69 of the sleeve 68 threadedly engage the inner threads 25 of the annular leg portion 26 of the lower portion 20 of the main body 16. The sleeve 68 radially surrounds a portion of the legs 56, 58 of the yoke 50 and provides stabilization of the yoke 50 during displacement thereof. Disposed radially inwardly of the legs 56, 58 of the yoke 50 and axially downwardly of the main body 16 is a body extension 74. The body extension 74 has a threaded top portion 75 that is adapted to threadedly engage the threaded opening 30 of the main body 16, and a threaded bottom portion 92 on the axial end of the body extension 74 opposite the threaded top portion 75. A bore 76 extends the longitudinal length of the body extension 74 and at the threaded top portion 75 is in fluid communication with the transverse passage 32.

As further discussed hereinbelow with reference to FIG. 6, a cylinder body 78 is threadedly coupled to the threaded bottom portion 92 of the body extension 74. A valve assembly 80 is disposed between the body extension 74 and the cylinder body 78. Threadedly attached to the threads 57 and 59 of respective legs 56 and 58 is an end cap 72 that retains a piston 70.

Figure 6:
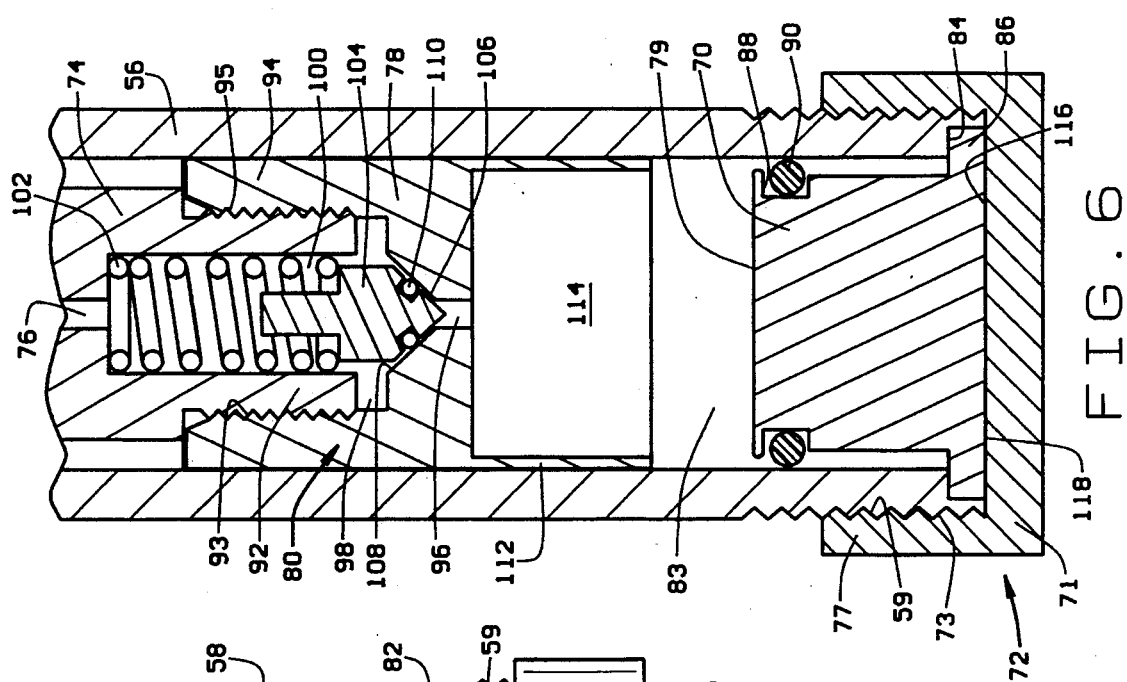
FIG. 6 is an enlarged partial sectional front view of the yoke, piston, and cylinder of the present invention depicted in an open position.

With reference now to FIG. 6, the structure of the lower portion of the sampler 10 will be described. The cylinder body 78 has a ring-shaped top portion 94 that includes inner threads 95 that engage the threads 93 of the lower portion 74. On the end opposite the top portion 94 the cylinder body 78 includes an annular wall 112 that defines a cylinder chamber 114. A centrally disposed, axially extending aperture 96 in the cylinder body 78 provides communication between the cylinder chamber 114 and the passage 76. At the axial end of the lower threaded portion 92, the passage 76 has a wider diameter portion 100 in which is disposed a spring 102 of the valve assembly 80. A valve head 104 abuts the spring 102 and is axially biased thereby. The cylinder body 78 and the lower threaded portion 92 define a chamber 98 that is axially adjacent the aperture 96 and in which the valve head 104 extends. The valve head 104 has a conical end surface 106 in which a resilient seal 110 is disposed. In its normally biased state, the conical end surface 106 and seal 110 of the valve head 104 contact and seat against a mating conical seating surface 108 that begins at and radially upwardly extends from the aperture 96. The seal 110 prevents fluid from entering the chamber 98 and thus the passage 76 when a sample is not being taken. It should be appreciated that other valve structures may be utilized rather than the valve structure that is pictured. For example, a rubber ball or the like may be used rather than the valve head and seal structure.

The piston 70 is disposed axially below the cylinder body 78 and is retained at the end of and between the leg portions 56, 58 of the yoke 50 by the end cap 72. The end cap 72 has a bottom disk portion 71 with a transverse annular wall portion 77. The wall portion 77 includes threads 73 that engage the threads on the leg portions 56, 58 of the yoke 50. The piston 70 has a disk portion 86 that abuts a cutout portion 84 disposed on the radial inside of the leg portions 56, 58. The top surface 118 of the end cap 72 contacts the lower surface 116 of the piston disk portion 86, thereby retaining and maintaining the piston 70 at the end of the yoke 50. Thus as is apparent, since the piston 70 is coupled to the yoke 50, axial displacement of the yoke 50 results in the axial displacement of the piston 70. The yoke 50 moves relative to the body 16 of the sampler as the body 16 is fixed to the pipe 14. Located proximate the top surface 79 of the piston 70 is an annular groove or channel 88 in which is disposed an elastomeric O-ring 90. The O-ring 90 provides a fluid tight seal with the annular wall 112 to prevent leakage of the sample around the sides of the piston 70 when a sample is being taken as described hereinbelow.

Figure 2:
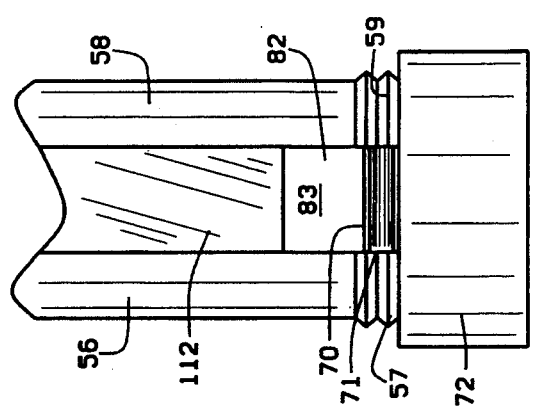
FIG. 2 is an enlarged partial front view of the yoke and piston assembly taken along line 2—2 of FIG. 1.

As depicted in FIG. 1 the end of the yoke 50, generally at least from the valve structure 80 axially downwardly, is disposed within the fluid flow of the pipeline 14. The sampler 10 is oriented within the pipeline 14 such that a flow-through opening 82, defined by the opposite spaces between the leg portions 56, 58 is in line with the flow of fluid through the pipeline. Referring to FIG. 2, the flow-through 82 is depicted. An interior chamber 83 is defined radially inwardly of the legs 56, 58, axially upwardly of the top surface 71 of the piston 70, and axially downwardly of the cylinder 114. In this manner, when the sampler 10 is in the non-sampling state as depicted in FIG. 6, the fluid flowing within the pipeline 14 may unimpededly flow through the flow-through opening 82 in one side and the flow-through opening (not shown) and the chamber 83.

With reference now to FIG. 9, there is depicted an alternative embodiment of the piston, the end cap structure, and the cylinder body. Because dirt and grit may be present in varying amounts in the fluid flowing within the pipeline, some of these particulates would naturally enter the flow-through 82 and chamber 83 of the sampler 10. The particulates may interfere with the operation of the sampler. Accordingly, the sampler depicted in FIG. 9 includes a smaller diameter piston 130 having an annular groove 132 in which is maintained an elastomeric O-ring 134. At the axial end of the piston opposite to the O-ring 134, a piston disk 136 radially extends therefrom in like manner to the piston disk 86 of sampler 10 (FIG. 6). The radial edge of the disk 136 is retained by the annular slot 84. Disposed in the disk 136 are a plurality of openings, of which two such openings 138 and 139 are shown. The end cap 140 is best depicted in FIG. 10 and includes a center portion 144 that roughly corresponds in diameter to the piston 130 and an outer annular ring portion 142. In this embodiment there are four arms 146, 147, 148, and 149 that radiate from the center portion 144 and connect with the outer annular portion 142. The center portion 144, arms 146–149, and the outer annular portion 142 defines four openings 150, 151, 152, and 153. The openings 150–153 correspond in shape and relative location to the piston disk openings. As can be appreciated the number of openings may vary, while such openings still provide a means of allowing the particulates to exit from the interior chamber 83. In this manner, the particulates do not accumulate within the interior chamber 83 which could possibly degrade the sample taking.

In order to accommodate the smaller diameter piston 130, a cylinder body 120 having an upper portion 122 with inner threads 123 is threadedly attached to the lower portion 92 of the body extension 74. The cylinder body 120 includes a lower cylindrical portion 126 that defines a cylinder cavity 128. An aperture 129 provides communication between the cylinder cavity 128 and the valve chamber 98. The cylinder cavity 128 is sized to accommodate the piston 130 such that the O-ring 134 provides a fluid tight seal during sampling.

Figure 11:
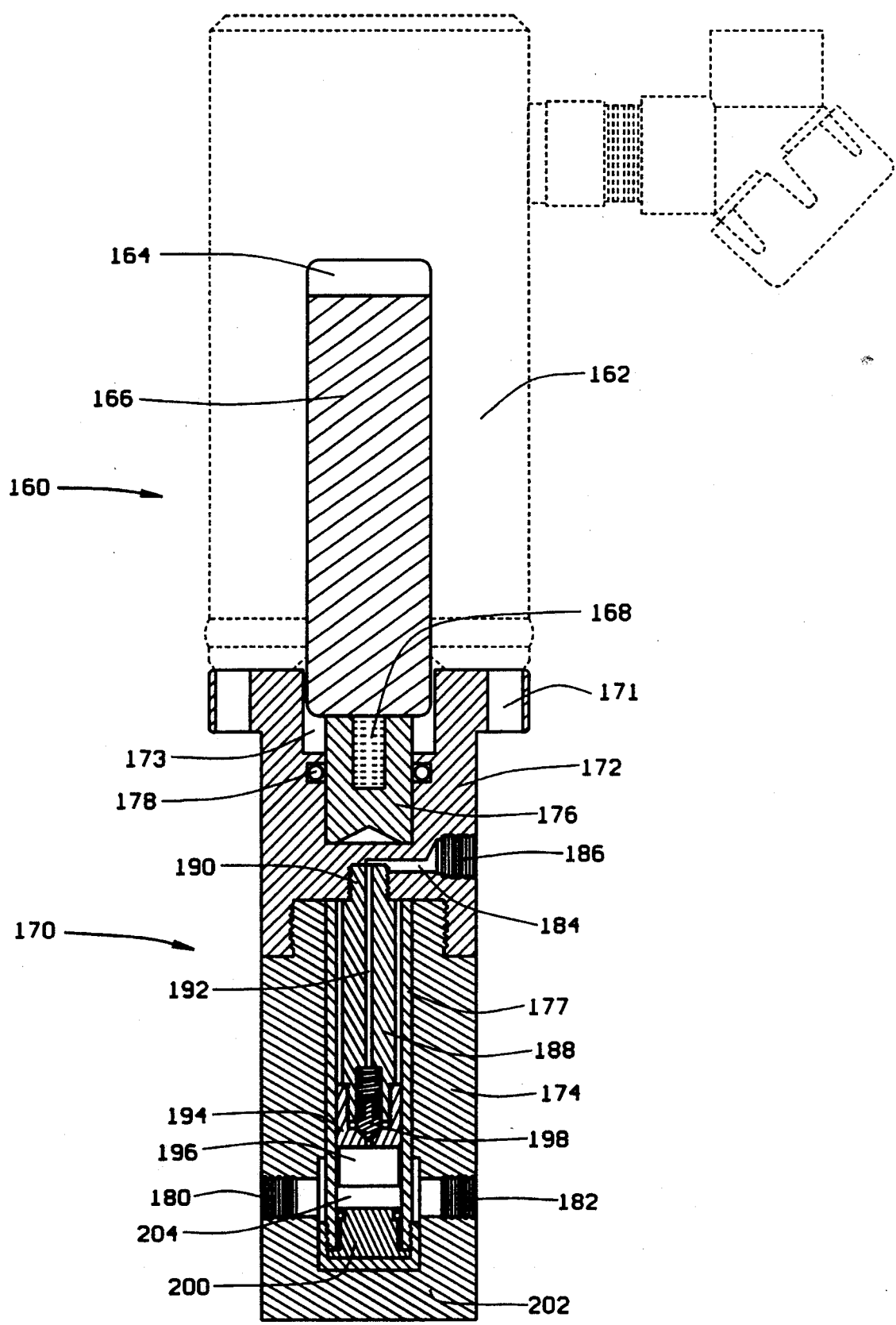
FIG. 11 is a front sectional view of a by-pass type sampler in accordance with an alternative embodiment of the present invention.

Referring now to FIG. 11 there is shown an alternative embodiment of a sampler generally designated 160. The sampler 160 is known as a by-pass type sampler in that the sampler itself is not disposed within the pipeline fluid flow, but is in fluid communication with the pipeline fluid flow via a conduit, tube, or the like. It should also initially be understood that many of the components of the sampler 160 are similar, if not identical, to the sampler 10 depicted in FIG. 1. The components of the sampler 160 have reference numbers that are different than the reference numbers of the sampler 10 of FIG. 1 even though some of the components are identical in form and function. However, where the components of the sampler 160 are different than the sampler 10, the differing components will be particularly described. Also, it should be appreciated that the alternative embodiment of the piston and end cap structure depicted in FIGS. 9 and 10 is equally suitable for use in the sampler 160 of FIG. 11.

The sampler 160 includes a body 170 that consists of an upper body portion 172 onto which is coupled a solenoid 162 by screws or the like through bores 171, and a lower body portion 174. The solenoid 162 has a shaft bore 164 in which is movably disposed a shaft 166. An axial end of the shaft 166 extends into a first cavity 173 of the upper body portion 172 and is coupled to a yoke 176. An O-ring 178 provides a seal around the yoke 176. The upper body portion 172 includes a passage 184 that is oriented transverse to the longitudinal axis of the upper body portion 172 and terminates in a threaded outlet 186.

The yoke 176 includes two legs of which only one leg 177 is shown in FIG. 11. The legs axially extend from the upper body portion 172. The yoke 176 extends through the upper body portion 172 in the same manner as the sampler 10. At the end of the yoke 176 is a piston 200 retained by an end cap 202. A body extension 188 having a central bore 192 that is in fluid communication with the transverse passage 184, includes a threaded top portion 190 that threadedly engages the upper body portion 172. A valve assembly 198 is disposed in the axial end of the body extension 188 that is opposite the threaded top portion 190 and is retained by a cylinder body 194. The cylinder body 194 also defines a cylinder chamber 196 that is adapted to receive the piston 200.

A threaded end of the lower body portion 174 engages the upper body portion 172 and radially surrounds the legs of the yoke 176 and the end cap 202. The lower body portion 174 has a first threaded bore 180 that is disposed adjacent the flow-through opening between the legs of the yoke 176. The first threaded bore 180 is adapted to receive an end of a threaded conduit, and can be considered an inlet wherein fluid is diverted from the pipeline and directed into the first threaded bore 180. Oppositely disposed to the threaded bore 180 is a second threaded bore 182 that is likewise adapted to be coupled to a threaded conduit which serves as the outlet for the fluid flow during non-sampling. Thus, the sampler 160 is configured to be mounted external to the pipeline.

OPERATION

Figure 7:
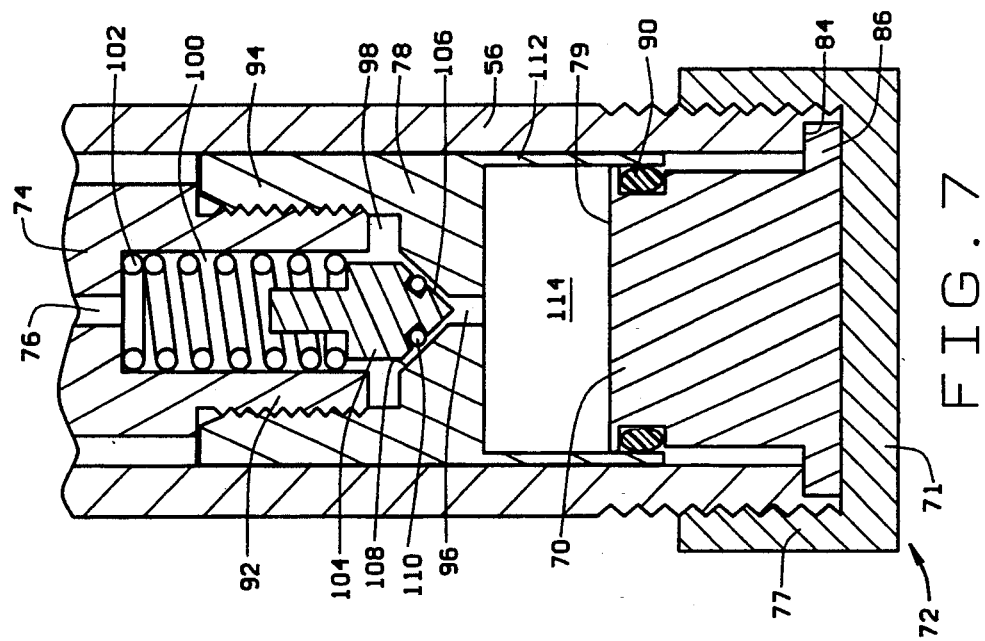
FIG. 7 is an enlarged partial sectional front view of the yoke, piston, and cylinder of the present invention in an initial stage of sample taking.

The operation of the sampler 10 will now be described with particular reference to FIGS. 6–8. It should be understood that the manner of operation is applicable to all of the embodiments discussed herein and is not directed only to the embodiment depicted in FIG. 1. However, when the components discussed below are not present in FIGS. 6–8 reference should be made to FIG. 1. FIG. 6 shows the sampler 10 is an open or pre/post-sampling stage wherein the fluid to be sampled is allowed to freely flow through the flow-through 82 and chamber 83. When a sample is to be taken, a signal is sent to the solenoid 60 whereby the solenoid shaft 64 is upwardly pulled. The pulling action of the shaft 64 likewise upwardly pulls the yoke 50 since the shaft 64 is coupled to the yoke 50 as described above. As the yoke 50 axially upwardly moves, the piston 70 is caused to axially upwardly move therewith since the piston 70 is coupled to the legs 56, 58 of the yoke 50. The yoke 50 and piston 70 move relative to the body extension 74 and cylinder body 78 since the body extension 74 and the cylinder body 78 are fixed to the body 16 and the body 16 is fixed to the pipe 14.

Upon initial axial upward displacement of the piston 70, the valve assembly 80 remains in a closed position. Additionally referring to FIG. 7, the sampler 10 is shown initiating, or alternatively returning from, a sampling operation. As the piston 70 axially upwardly travels, the flow-through 82 is closed off by the sidewalls of the piston 70, while the chamber 83 vanishes. The fluid within the chamber 83 is necessarily forced into the cylinder 114. As the piston 70 enters the cylinder 114, the O-ring 90 is compressed against the inner annular wall of the portion 112 defining the cylinder 114. This protects against leakage of the sample from the cylinder 114 to ensure that a known volume of sample is taken every sampling operation. As the piston 70 enters the cylinder 14, the head 104 of the valve assembly 80 unseats by the rising pressure due to the compression of the sample by the displacing piston 70. As the head 104 unseats, the sample now trapped within the cylinder 114 flows into the aperture 96 and around the head 104.

Referring additionally to FIG. 8, as the piston 70 reaches its end of travel or stroke, the cylinder 114 volume capacity is essentially reduced to zero, and the trapped sample must flow axially upwardly through the spring chamber 100, into the axial passage 76, and out passage 32. Coupled to passage 32 via threaded outlet 34 is a conduit (not shown) that is in fluid communication with a storage vessel (not shown). With the present sampler, any type of pressurized or non-pressurized storage vessel may be used.

After sampling, the solenoid shaft 64 and thus the yoke 50 and piston 70 returns to its rest state as shown in FIG. 6 and is ready for another sampling operation. Because only the yoke and piston move relative to the cylinder, the present sampler is less likely to clog or require often maintenance.

It should be understood that the sampling procedure takes place in a relatively short amount of time. However, within this short duration time interval, a sample of a predetermined volume is taken and stored.

While the foregoing is directed to the preferred embodiment of the present invention, other and further embodiments of the invention may be devised without departing from the basic scope thereof, and the scope thereof is determined by the claims which follow.

What is claimed is:

1. An assembly for obtaining a liquid or gas sample from a pipeline comprising:
   a body defining a first end and a second end, said body including a main passage extending from said first end to said second end;
   an outlet passage disposed in said body, said outlet passage adapted to be coupled to a sample storage vessel;
   a yoke disposed in said main passage and longitudinally movable therein relative to said body, said yoke having a first end and a second end, said second end of said yoke extending beyond said second end of said body and having a flow passage allowing communication with an interior of said yoke;
   a pulling solenoid disposed adjacent said first end of said body, said pulling solenoid including a solenoid shaft coupled to said first end of said yoke, said yoke movable by and with said solenoid shaft;
   a sleeve coupled to said second end of said body, said sleeve at least partially surrounding said yoke;
   an extension coupled to said second end of said body, said extension having a bore therethrough in communication with said outlet passage;
   a cylinder body coupled to an end of said extension remote from said second end of said body, said cylinder body defining a cylinder in communication with said extension bore; and
   a piston disposed at said second end of said yoke, said piston adapted to be received into said cylinder to inject a volume of sample flowing in the pipeline and through said flow passage when displaced by said yoke upon actuation of said solenoid shaft.

2. The assembly of claim 1, further comprising:
   a check valve disposed in said body extension bore at one end of said body extension.

3. The assembly of claim 1 wherein:
   a length of said main passage is defined by a first arcuate portion and a second arcuate portion disposed radially opposite said first arcuate portion; and said second end of said yoke defined by a first arcuate leg portion and a second arcuate leg portion disposed radially opposite said first arcuate leg portion, said first and second arcuate leg portion of said yoke dimensionally corresponding to said first and second arcuate portion of said main passage and adapted to be received therethrough.

4. The assembly of claim 3, wherein:

said first and second arcuate portions of said main passage define a center portion of said body, said outlet passage being transverse to said main passage and extending into said center portion, said extension coupled to said center portion.

5. An assembly for obtaining a fluid sample from a fluid flowing in a pipeline comprising:

a main body defining a first end and a second end;

a yoke bore extending from said first end to said second end of said main body, at least a length of said yoke bore defined by radially oppositely disposed first and second slots;

an outlet passage disposed in said main body;

a yoke reciprocatingly disposed in said yoke bore, said yoke having a first prong and a second prong adapted to be received in said first and second slots, said first and second prongs projecting beyond said second end of said main body;

a pulling solenoid disposed at said first end of said main body, said pulling solenoid having a shaft that is actuatably reciprocable and coupled to said yoke;

a body extension coupled to said second end of said main body radially inwardly of said first and second prongs of said yoke, said body extension having an outlet bore therethrough in communication with said outlet passage;

a cylinder coupled to an end of said body extension remote from said second end of said main body, said sample cylinder having a restricted opening therein in communication with said outlet bore of said body extension;

a piston coupled to an end of said first and second prongs and adapted to be received in said cylinder to inject a volume of sample therein when said yoke is upwardly moved by said solenoid shaft; and a flowthrough passage in said first and second prongs permitting the fluid flowing in the pipeline to flow therethrough.

6. The assembly of claim 5, wherein:

said first and second slots are each arcuate shaped; and said first and second prongs are each arcuate shaped.

7. The assembly of claim 5 further comprising:

a valve disposed between said outlet bore of said body extension and said restricted opening of said cylinder, said valve normally biased closed but which opens upon the injection of a sample into said cylinder by upward movement of said piston.

8. The assembly of claim 5, wherein said first and second slots define a center portion, said outlet passage being transverse to said yoke bore and extending into said center portion, said body extension coupled to said center portion.

* * * * *